(12) United States Patent
Baid

(10) Patent No.: US 9,844,626 B2
(45) Date of Patent: Dec. 19, 2017

(54) IV FLOW RATE REGULATOR AND METHOD OF ITS FABRICATION

(75) Inventor: Rishi Baid, New Delhi (IN)

(73) Assignee: POLY MEDICURE LIMITED, Faridabad (IN)

( * ) Notice: Subject to any disclaimer, the term of this patent is extended or adjusted under 35 U.S.C. 154(b) by 1151 days.

(21) Appl. No.: 13/825,212

(22) PCT Filed: Sep. 1, 2011

(86) PCT No.: PCT/IB2011/053830
§ 371 (c)(1),
(2), (4) Date: Mar. 20, 2013

(87) PCT Pub. No.: WO2012/038847
PCT Pub. Date: Mar. 29, 2012

(65) Prior Publication Data
US 2013/0178805 A1 Jul. 11, 2013

(30) Foreign Application Priority Data
Sep. 21, 2010 (IN) .......................... 2254/DEL/2010

(51) Int. Cl.
*A61M 5/168* (2006.01)
(52) U.S. Cl.
CPC .... *A61M 5/16804* (2013.01); *A61M 5/16877* (2013.01); *A61M 5/16881* (2013.01); *A61M 2207/00* (2013.01); *Y10T 29/49405* (2015.01)
(58) Field of Classification Search
CPC .......... A61M 2207/00; A61M 5/16804; A61M 5/16877; A61M 5/16881; Y10T 29/49405
See application file for complete search history.

(56) References Cited

U.S. PATENT DOCUMENTS

| | | | |
|---|---|---|---|
| 3,877,428 A | 4/1975 | Seagle et al. | |
| 4,335,729 A | 6/1982 | Reynolds et al. | |
| 5,009,251 A * | 4/1991 | Pike ................. | A61M 5/16881 137/561 A |
| 5,234,413 A | 8/1993 | Wonder et al. | |
| 6,921,389 B2 * | 7/2005 | Scagliarini ........ | A61M 5/16881 251/208 |

(Continued)

OTHER PUBLICATIONS

PCT International Search Report; Applicant: Poly Medicure Limited; International Application No. PCT/IB2011/053830; Date of Actual Completion of International Search: Feb. 2, 2012; dated Feb. 13, 2012; Authorized Officer: Turkavci, Levent.

*Primary Examiner* — Imani Hayman
(74) *Attorney, Agent, or Firm* — Bodi Law LLC

(57) ABSTRACT

An IV flow rate regulator for precision dosage of medical liquids including a first part, a second part with an integrated outlet tubular connector and a mating attachment part with an integrated inlet tubular connector, coupled to one another in a rotatable manner with a first elastic gasket in a depression in the base wall of the second part, a second elastic gasket in a depression in the base wall of the mating attachment part, a dosing passage groove provided between the first and second gaskets, the dosing groove opening progressively the communication between the inlet tubular connector and the outlet tubular connector by rotation of the first and second parts. Also provided is a method for the fabrication of the IV flow regulator.

6 Claims, 10 Drawing Sheets

(56) References Cited

U.S. PATENT DOCUMENTS

| | | | |
|---|---|---|---|
| 7,624,749 B2 * | 12/2009 | Guala | A61M 5/16813 116/277 |
| 2004/0261872 A1 | 12/2004 | Mermet | |
| 2009/0192472 A1 | 7/2009 | Bettini et al. | |
| 2010/0198167 A1 * | 8/2010 | Simon | A61M 5/14 604/248 |

* cited by examiner

IV FLOW RATE REGULATOR AND METHOD OF ITS FABRICATION

CROSS-REFERENCE TO THE RELATED APPLICATION

This application IS A U.S. national stage application of PCT application No. PCT/162011/053830 filed on Sep. 1, 2011, incorporated herein by reference, which claims priority from Indian Patent Application No. 2254/DEL/2010, filed on Sep. 21, 2010, the entire disclosure of which is incorporated herein by reference.

FIELD OF THE INVENTION

The present invention relates in general to the administration of medical liquids. More particularly, the present invention relates to an IV flow rate regulator for precision dosage of said liquids and the method of its fabrication.

BACKGROUND OF THE INVENTION

There are a number of fluid-flow, particularly liquid-flow, regulating devices for the control of the rate of flow of a gravity-fed or gravity-assisted fluid-delivery system in medical applications. Such flow-control devices and regulators are particularly useful for delivery of liquids, such as intravenous fluids or other fluids, in medical applications.

However, such known devices, while effective, are often quite complicated in construction and operation. Further, such devices are not easily and simply manufactured. Robust, high volume production of a precision dosage compensating flow control regulator has proved to be extremely challenging.

Thus, there is a constant need for an IV flow rate regulator for precision dosage of medical liquids which is simple and economical in construction, fabrication and its use.

SUMMARY OF THE INVENTION

In one aspect of the invention, there is provided an IV flow rate regulator for precision dosage of medical liquids comprising a first part, a second part with at least one integrated outlet tubular connector and a mating attachment part with at least one integrated inlet tubular connector, said first, second and mating attachment parts made of moulded plastic material and being coupled to one another in a rotatable manner about an axis of rotation with a first gasket made of elastomeric material being inter-positioned in a depression integrally made in the base wall of said second part, a second gasket made of elastomeric material being inter-positioned in a depression integrally made in the base wall of said mating attachment part, at least one dosing passage groove being provided between said first and second gaskets, said dosing groove opening progressively the communication between said inlet tubular connector and said outlet tubular connector by means of the relative rotation of said first and second parts.

Also forming the subject of the invention is a method for the fabrication of the IV flow regulator comprising the following steps: moulding said first part, said second part and said mating attachment part within a first, second and third mould respectively; moulding said first gasket and said second gasket as whole with annular legs; positioning said first gasket in the depression formed integrally in the base wall of said second part in a position, the first surface of said first gasket facing the first part; positioning said second gasket in the depression formed integrally in the base wall of said mating attachment part in a position, the first surface of said second gasket facing the first part; fitting said first part, said second part and said mating attachment part to one another in a mutually rotatable way aligning the thorough holes made in said first part, said second part, said mating attachment part, said first gasket and said second gasket coaxially in a see through arrangement; fitting the first tubing line to said inlet tubular connector and second tubing line to said outlet tubular connector.

It is thus a primary object of this invention to provide an IV flow rate regulator for precision dosage liquids which is simple and economical in construction, fabrication and use.

Another object of this invention is to provide an IV flow rate regulator for delivering a liquid for administration to a patient and maintaining a selected rate of flow as per the peripheral side scale.

Another object of this invention is to provide an IV flow rate regulator which maintains a selected rate of flow with precision dosage in spite of changes in pressure within the liquid.

Yet another object of this invention is to simplify the fabrication of the IV flow rate regulator defined above so as to reduce appreciably the costs of production, storage as well as design structure thereof.

These and other objects of the present invention, as well as many of the attendant advantages thereof, will become more readily apparent when reference is made to the following description, taken in conjunction with the accompanying drawings.

BRIEF DESCRIPTION OF THE DRAWINGS

The present invention will now be described in detail with reference to the accompanying drawings, which are provided by way of non-limiting examples and in which.

DETAILED DESCRIPTION OF THE INVENTION

The embodiments of the present invention relate to an IV flow rate regulator 10 for precision dosage of medical liquids and the method of its fabrication.

With reference to the drawings, a preferred embodiment of an IV flow rate regulator 10 for precision dosage of liquids is shown. The IV flow rate regulator 10 is a gravity-flow regulator and preferably is a disposable, single-use device provided to the user in a sterilized package.

Figure 1:
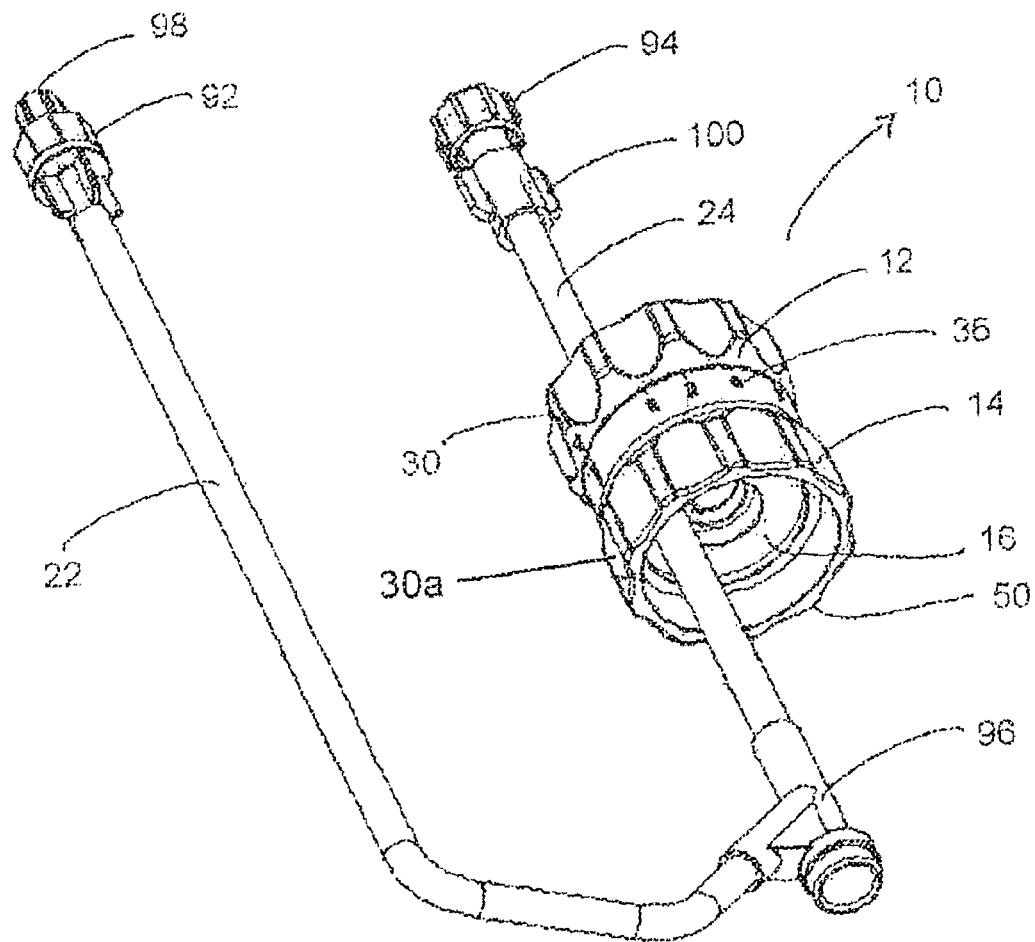
FIG. 1 illustrates a schematic perspective view of the IV flow rate regulator according to the invention.
Figure 2:
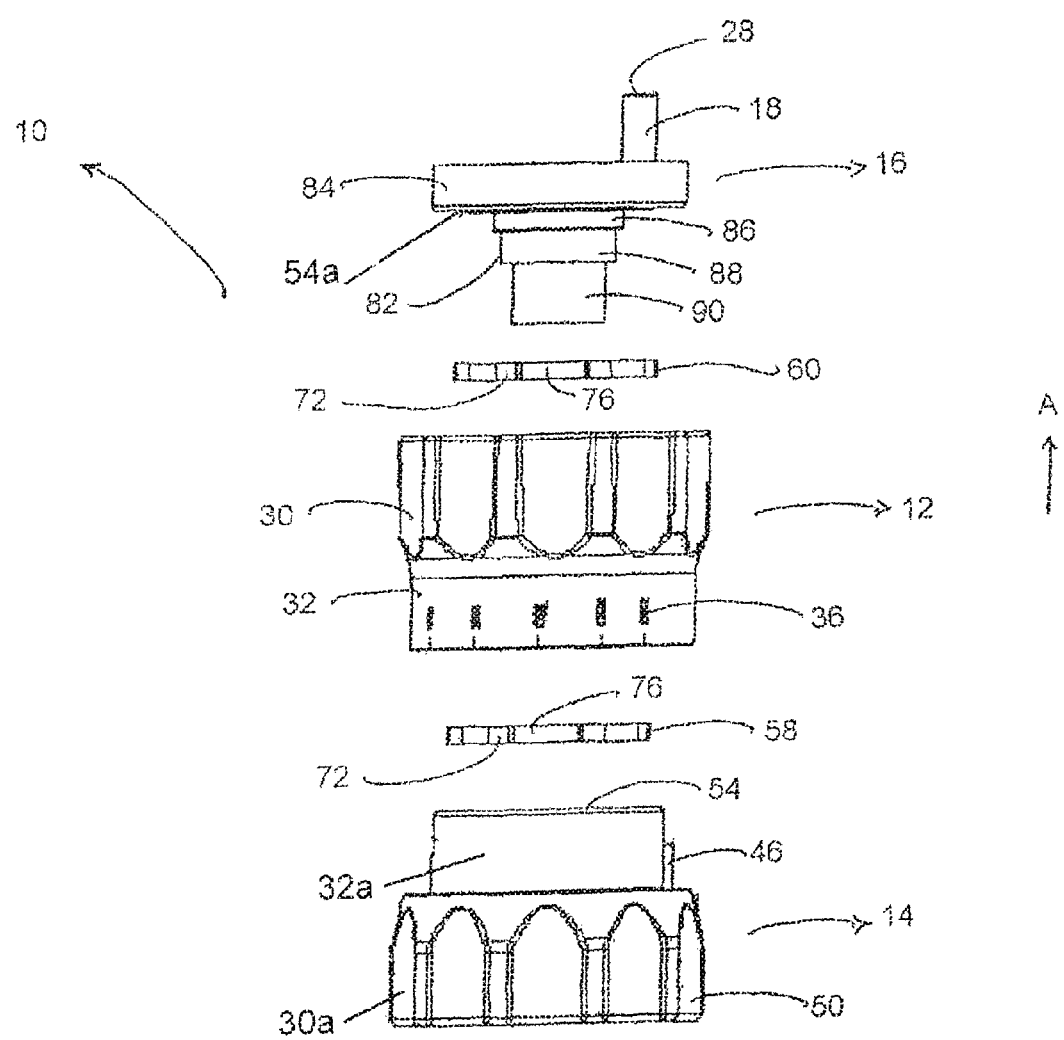
FIG. 2 illustrates an exploded front view of the IV flow rate regulator according to the invention.
Figure 3:
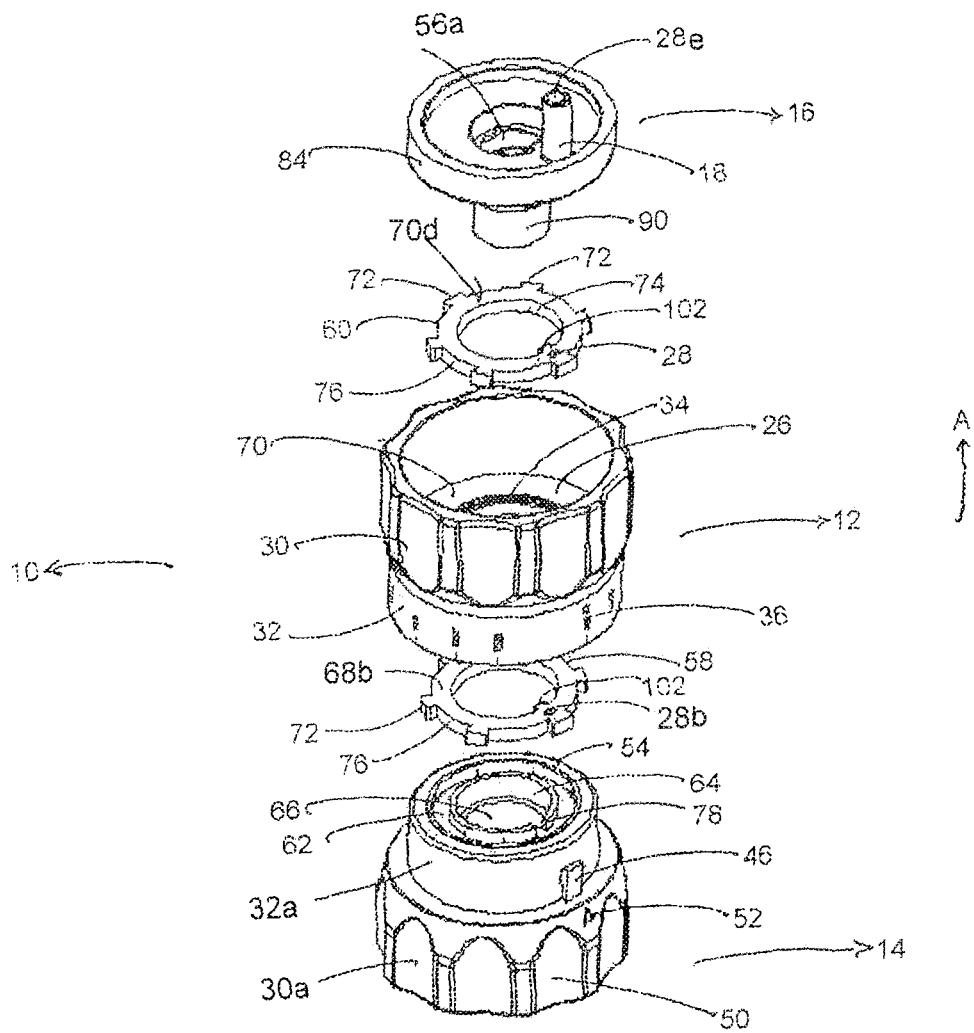
FIG. 3 illustrates an exploded perspective view of the IV flow rate regulator according to the invention
Figure 3A:
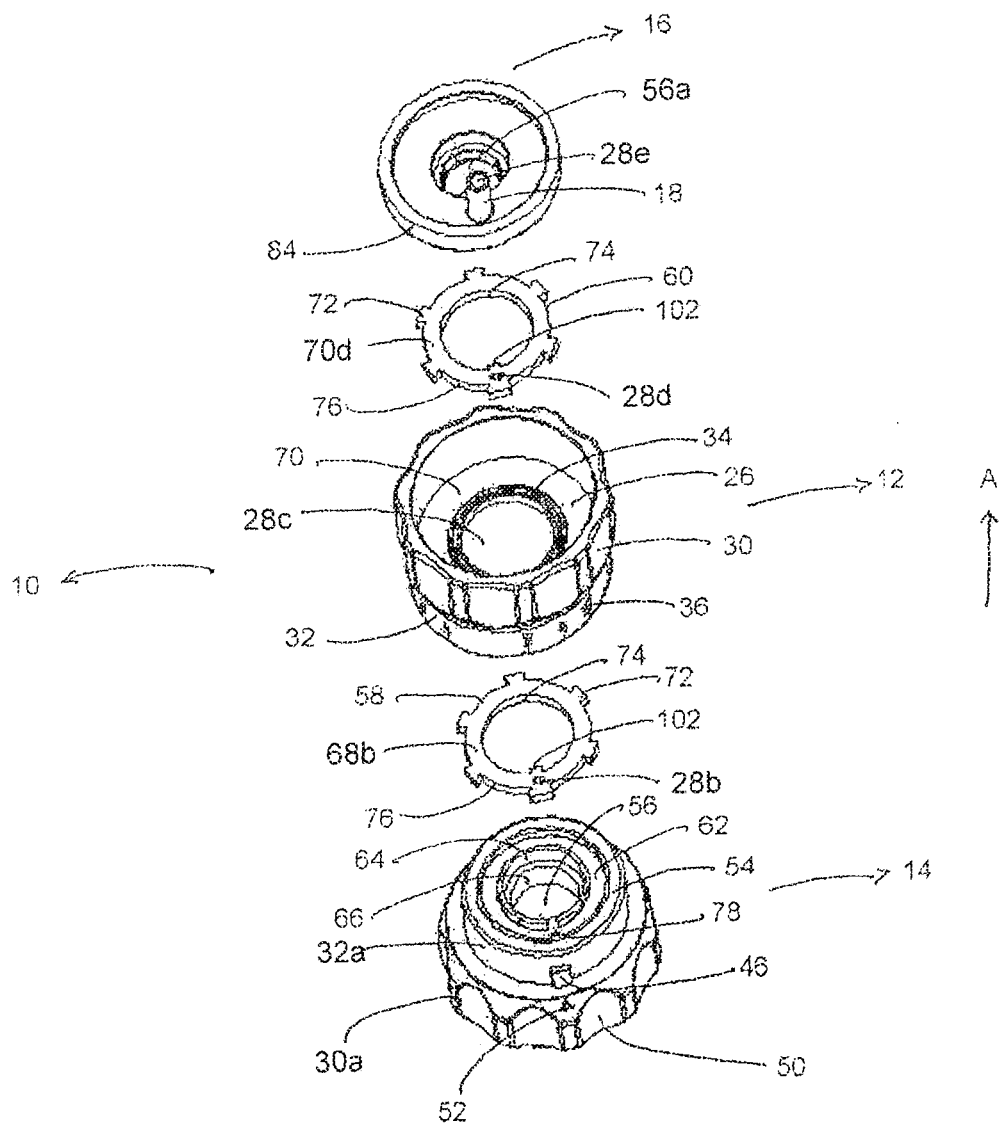
FIG. 3a illustrates another exploded perspective view of the IV flow rate regulator according to the invention
Figure 3B:
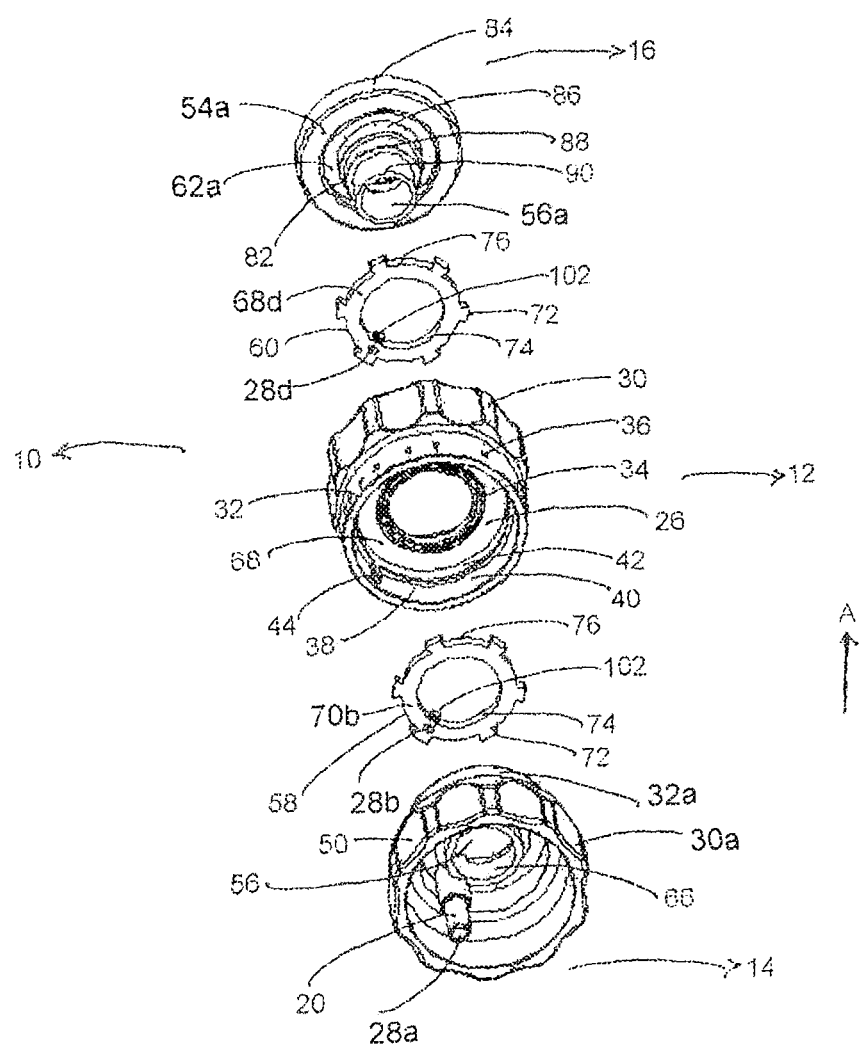
FIG. 3b illustrates another exploded perspective view of the IV flow rate regulator according to the invention
Figure 3C:
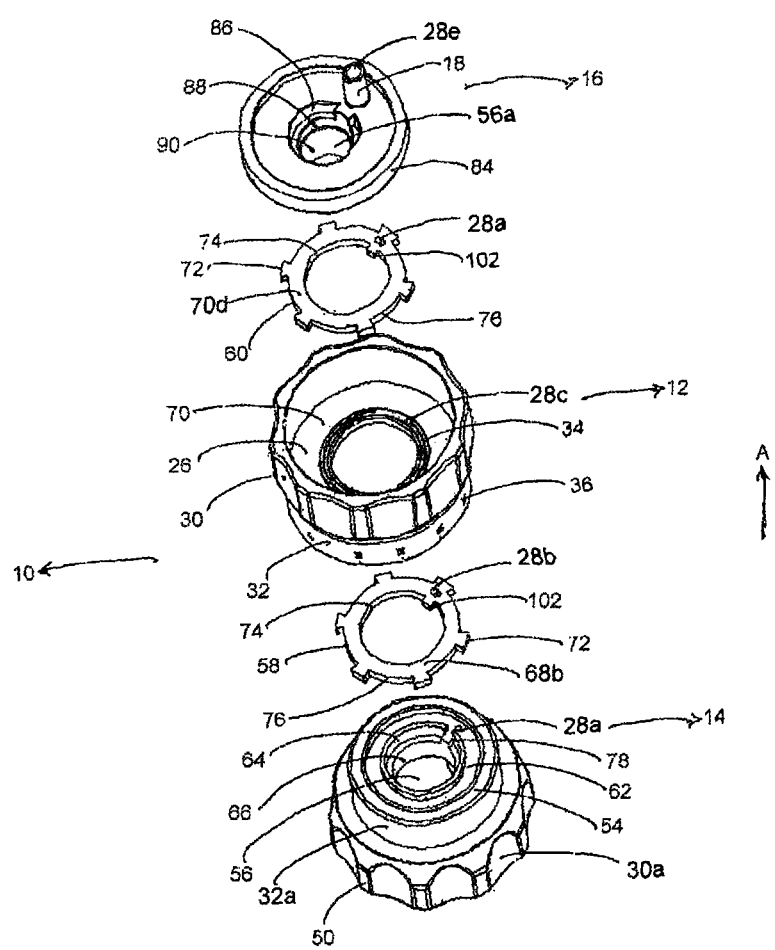
FIG. 3c illustrates another exploded perspective view of the IV flow rate regulator according to the invention
Figure 4:
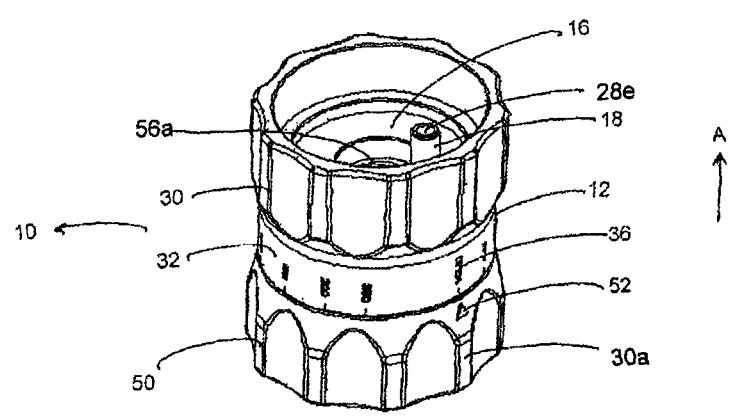
FIG. 4 illustrates a perspective view of the IV flow rate regulator according to the invention.

Referring to FIG. 1, an IV flow rate regulator 10 according to the invention is illustrated overall. In use (not shown) the flow regulator 10 is deployed at a location between an IV fluid source and the patient. It comprises a first part 12, a second part 14 and a mating attachment part 16 in a connecting arrangement to said first 12 and second part 14. An integrated inlet tubular connector 18 formed in the mating attachment part 16 connects the inlet of the flow regulator 10 to the first flexible tubing line 22. Likewise, an integrated outlet tubular connecter 20 formed in the second part 14 connects the outlet of the flow regulator 10 to the second flexible tubing line 24. In use, (not shown here) the first tubing line 22 is connected to an IV fluid source and the second tubing line 24 carries the liquid stored in the fluid source to a patient.

As shown, the first 22 and second tubing lines 24 are provided with integrated luer connectors having a male member 92 and female member 94. The male luer 92 connector configured to receive a luer cap 98 at its distal end connects the first tubing line 22 to the fluid source and the female luer connector 94 being provided with a luer lock 100 connects the second tubing line 24 to the IV catheters or other IV related devices. An auxiliary line is also provided into the first tubing line 22 at distal end by means of an integrated Y-site 96. In addition, the Y-site 96 has a needle connection in the form of a rubber diaphragm which serves as an intermittent injection site.

Referring now to FIGS. 2, 3, 3a, 3b, 3c, 4 and 5, an IV flow rate regulator 10 according to the invention has parts consisting of components, viz. a first part 12, a second part 14 and a mating attachment part 16. These components are preferably fabricated by injection moulding using a suitable grade plastic material such as, for example, medical grade plastic or polymeric material. In FIGS. 2, 3, 3a, 3b, 3c and 5, although the components of the flow rate regulator 10 are shown as separate components for ease of fabrication and assembly, they are unitary with each other when in use.

The first part 12 is preferably made of moulded plastic material and comprises in a single piece a substantially circular wall 26 with formation of a hole 28c facilitating a space to receive the connecting element 82 of the mating attachment part 16. The circular wall 26 is formed integrally with a side skirt 30 extending upwardly from said circular wall 26 and a side wall 32 extending downwardly from said circular wall 26 in an axial direction identified with "A". The circular wall 26 is provided with a first surface 68 and a second surface 70 (opposite the first) being in a position corresponding to the face thereof set facing a base wall 54 of the second part 14 and a base wall 54a of the mating attachment part 16 respectively when assembled. Further, the circular wall 26 comprises at least one dosing groove 34 on each of the first 68 and second surfaces 70 of the circular wall 26 in communication with the inlet tubular connector 18 integrally made in the mating attachment part 16 and with the outlet tubular connector 20 made integrally in said second part 14.

The side wall 32 of the first part 12 is formed integrally with at least one peripheral scale as a whole in a circular fashion with different units of measurements of the flow of liquid that, in use, traverse the flow regulator 10, entering the inlet connector 18 and exiting through the outlet connector 20. Also on the side wall 32 of the first part 12 integrally formed on the peripheral scale 36 are wordings indicating the condition of the initial opening and complete closing of the flow regulator 10.

The inner surface of the side wall 32 of the first part has a generally cylindrical shape comprising plurality of walls, for example, defined by wall (A) 40 and wall (B) 42 of varying dimensions. In order to provide a positive indication of the "off" position so that a low rate of fluid flow is not inadvertently delivered to the patient, the flow regulator 10 is provided with projection feature. The inner surface of the side wall 32 is provided with at least one first projection 44 in wall (A) 40 which engages with at least one second projection 46 provided on the outer surface of the side wall 32 of the second part 14 of the flow regulator 10 when in use. When first part 12 is assembled into second part 14, wall (B) 42 of the first part 12 rests on the second projection 46 provided on the outer surface of the side wall 32 of the second part 14 of the flow regulator 10.

The engagement of the first projection 44 and second projection 46 controls the condition of the initial opening and complete closing of the flow regulator 10. When a control dial 50 of the second part 14 having a pointer 52 is rotated counterclockwise to the "off" position, the second projection 46 will encounter the first projection 44 and the complete closing indicating the "off" position has been reached. Rotation in the opposite direction will cause the second projection 46 to abut the first projection 44 in the full "open" position. Thus, the control dial 50 of the second part 14 may be rotated approximately 360° from "off" to a full "open" position being integrally marked on the first part 12. The engagement of the first projection 44 and the second projection 46 is a light, frictional engagement so that as the control dial 50 is rotated, the user will sense the firm rotation as the projections 44, 46 abut each other. The engagement of projections 44, 46 will also assist in preventing inadvertent rotation of the dial 50. The definition of the flow rate of the liquid is indicated by the peripheral scale 36 marked on the side wall 32 of the first part 12 and by a pointer 52 provided on the side skirt 30a of the second part 14. The different length of the scale 36 indicates the different flow rates obtainable by means of the flow regulator 10. The side skirts 30 and 30a of the first 12 and second part 14, respectively, provide a perimetral gripping edge being designed to facilitate handling, operation and regulation easily by human hands.

The second part 14 likewise preferably made of moulded plastic material comprises in a single piece integrally a base wall 54, a side wall 32a, a side skirt 30a, a central bore 56 and a first gasket 58 positioned in the matching depression 62 integrally formed on the base wall 54 of the second part 14. The tubular outlet connector 20 projects axially in a direction opposite to "A" from the base wall 54 in a corresponding opening position of the side skirt 30a shaped ergonomically. The base wall 54 is formed, in a position corresponding to the face thereof set facing the circular wall 26 of the first part 12. The tubular outlet connector 20 made integrally in the second part 14 defines an outlet passage. The outlet connector 20 is generally cylindrical and is preferably sized to be connectable to the second flexible tubing line 24 as shown in FIG. 1. The outlet connector 20 projects axially from the base wall 54 of the second part 14 being formed integrally therewith. The base wall 54 of the second part 14 is formed, in a position corresponding to fit in with the first part 12 of the flow regulator 10. The base wall 54 has a thorough hole 28a in communication with the tubular outlet connector 20 which corresponds with a thorough hole 28*b* made in the first gasket 58 positioned in the second part 14.

The inner surface of the side wall 32*a* of the second part 14 with a central bore 56 has a generally cylindrical shape comprising plurality of walls, for example, defined by wall (C) 64 and wall (D) 66 of varying dimensions, which in assembled position engages the mating attachment part 16. The wall (C) 64 is provided with a projection 80 which engages with the matching depression (not shown) 62 formed in the wall (E) 86 and (F) 88 of the connecting element 82 of the mating attachment part 16.

The first gasket 58 is preferably flat and annular having dimensions corresponding to those of the substantially matching depression 62 made in the base wall 54 of the second part 14. The gasket 58 has a first surface 68*b* facing the first part 12 of the flow regulator 10, and a second surface 70*b* (opposite the first) capable of being positioned in the substantially matching depression 62 made in the base wall 54 of the second part 14 where it is positioned as shown in FIGS. 3, 3*a*, 3*b* and 3*c*. The base wall 54 of the second part 14 is provided with a spaced apart depression 62 so that the annular legs 72 of the first gasket 58 can be inserted in such depression 62. The gasket 58 is provided with at least one thorough hole 28*b* to the outlet passage of the tubular outlet connector 20. The thorough hole 28*b* is positioned in connection coaxially with the hole 28*a* formed in the base wall 54 of the second part 14 in communication with the tubular outlet connector 20.

Figure 7:
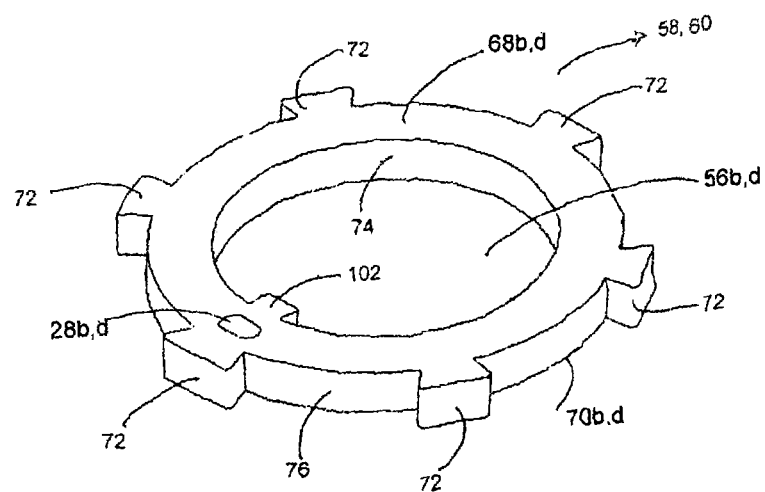
FIG. 7 illustrates a perspective view of the gasket according to the invention.
Figure 8:
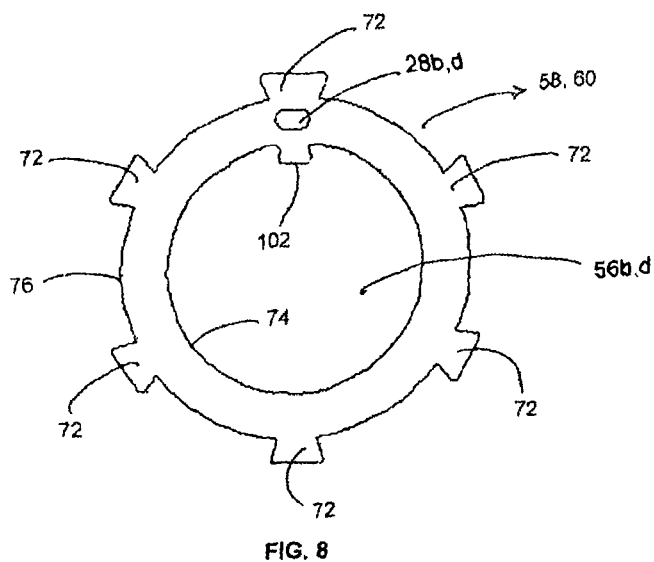
FIG. 8 illustrates a front view of the gasket according to the invention.

The first gasket 58 comprises plurality of annular legs 72 which project radially from the outer periphery 76 of the gasket 58 as shown in FIGS. 7 and 8. The gasket 58 is also provided with at least one leg 102 which project radially inward from the inner periphery 74 of the gasket 58. As shown in FIGS. 7 and 8. The leg 102 projecting from the inner periphery 74 of the gasket 58 helps in fitting the gasket 58 in the recess 78 formed in the wall (C) 64. The recess 78 is formed to engage the first gasket 58 substantially halfway over the projection 58 in the wall (C) 64. The first gasket 58 has a substantially circular shape with a hole 56*b* in the center to receive the connecting element 82 of the mating attachment part 16 facilitating the fixture of the first gasket 58 in the matching depression 62 formed in the base wall 54 of the second part 14.

Figure 5:
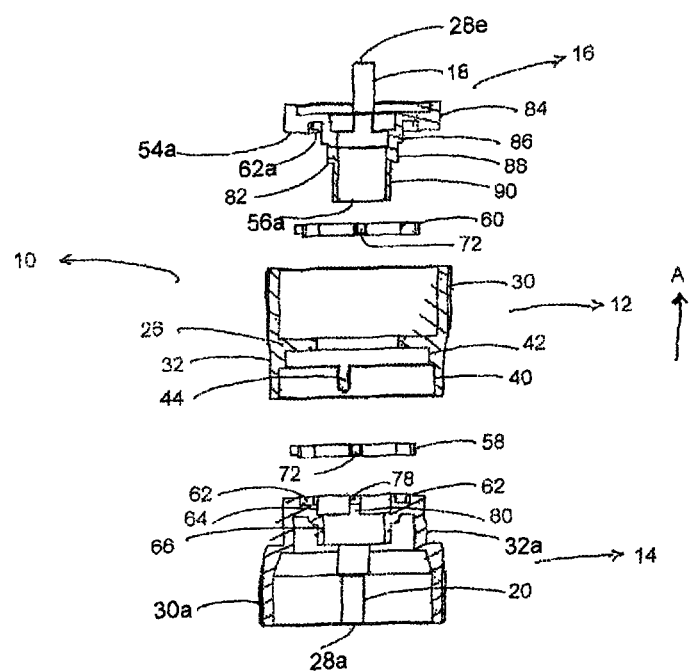
FIG. 5 illustrates an exploded cross-sectional view of the IV flow rate regulator according to the invention.

The mating attachment part 16 of the IV flow rate regulator 10, is also formed by, for example, injection moulding of a suitable plastic material comprises in a single piece comprising a base wall 54*a*, a plane dial shaped top wall 84, from which there projects axially in a direction defined by "A" the tubular inlet connector 18 and a central bore 56*a* forming the connecting element 82 which in assembled position connects the first part 12 and second part 14. The top wall 84 has a thorough hole 28*e* in communication with the tubular inlet connector 18 which opens thorough the second gasket 60. The connecting element 82 has a generally cylindrical shape comprising plurality of walls, for example, defined by wall (E) 86, (F) 88 and (G) 90 of varying dimensions. Walls (E) 86 and (F) 88 are provided with a depression 62*a* (not shown) to accommodate the projection 80 formed in wall (C) 64 of the inner surface 36 of the side wall 32*a* forming a central bore 56 in the second part 14. In the assembled position, as shown in FIG. 5, the connecting element 82 is arranged to be inserted into a connection counter-element of the second part 14. The counter-element in the second part 14 projects from an inner portion of the surface which defines a central bore 56 containing counter-element defined by walls (C) 64 and (D) 66. The connecting element 82 is hollow at its central formation.

The second gasket 60 has a first surface 68*d* facing the first part 12 of the flow regulator 10, and a second surface 70*d* (opposite the first) facing the mating attachment part 16 as shown in FIGS. 3, 3*a*, 3*b* and 3*c*. The second gasket 60 comprises plurality of annular legs 72 which project radially from the outer periphery 76 of the gasket 60. The gasket 60 is also provided with at least one leg 102 which project radially inward from the inner periphery 74 of the gasket 60. As shown in FIGS. 7 and 8 the leg 102 projecting from the inner periphery 74 of the gasket 60 helps in fitting the gasket 60 in the recess 78 (not shown) formed in the wall (E) 86. The recess 78 is formed to engage the second gasket 60 as anti-slip gripping element. The base wall 54*a* of the mating attachment part 16 is provided with spaced apart depression 62*a* so that the annular legs 72 of the second gasket 60 can be inserted in such depression 62*a*. The second gasket 60 is capable of being positioned in the substantially matching depression 62*a* made in the base wall 54*a* of the mating attachment part 16 where it is positioned in the assembled position.

The gasket 60 is provided with at least one thorough hole 28*d* corresponding to the inlet passage of the tubular inlet connector 18. The thorough hole 28*d* is positioned in connection coaxially with the hole 28*a* formed in the base wall 54 of the second part 14 in communication with the tubular inlet connector 18. The second gasket 60 has a substantially circular shape with a hole 56*d* in the center to receive the connecting element 82 facilitating the fixture of the second gasket 60 in the matching depression 62*a* formed in the base wall 54 of the mating attachment part 16.

When assembled and positioned in the matching depressions 62 and 62*a* said first 58 and second gaskets 60 and the annular legs 72 integrated therein ensure that they do not move out of the depression 62 and 62*a* formed integrally in the second part 14 and the mating attachment part 16 respectively and ensure the smooth and correct functioning of the IV rate flow regulator 10. The first 58 and second 60 gaskets are preferably made of suitable elastomeric material.

Figure 6:
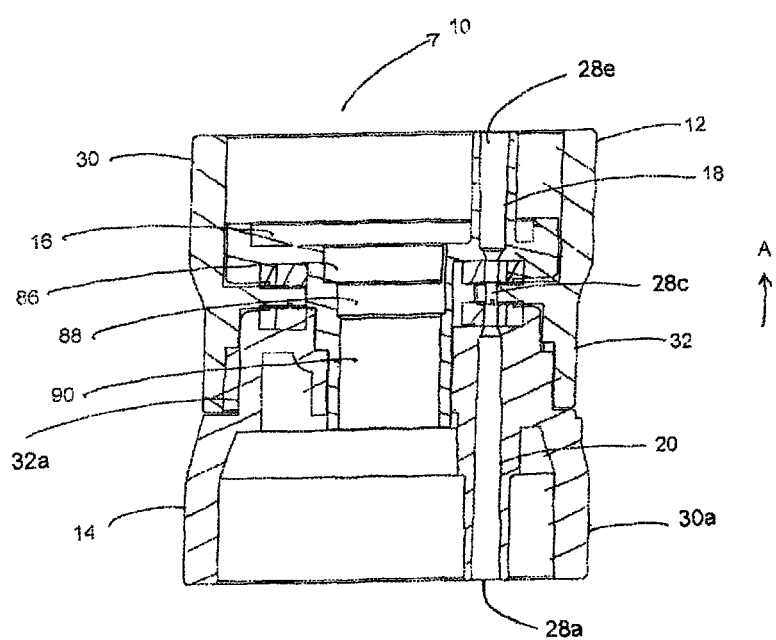
FIG. 6 illustrates another axial cross section of the IV flow regulator on the line X-X according to the invention.

The angular orientation of the inlet and outlet connectors 18, 20 provides significant functional advantages in that the angular orientation facilitates use of an easy-to-adjust dial having a large diameter. The flow rate variation is achieved by moving the second part 14 relative to the first part 12 about the axis X. As shown in FIG. 6, it will be assumed that the flow regulator 10 is in the open condition in which the hole 28*a* in the base wall 54 of the second part 14, hole 28*e* in the base wall 54 of the mating attachment part 16 and the hole 28*c* formed in the dosing groove passage 34 of the circular wall 26 of the first part 12 are coaxial forming a liquid passage flow line. The definition of the open condition can be taken as the position where the pointer 52 marked on the second part 14 indicates to the "open" position integrally marked on circular peripheral scale 36 of the first part 12. This open condition, can be understood of a position when, in this condition, the liquid passing from the first tubing line 22 into the inlet connector 18 of the mating attachment part 16 passes without varying its flow rate, into the hole 28*c* formed in the circular wall 26 of the first part 12 and from there into the outlet connector 20 of the second part 14 and travels to the patient from the second tubing line 24.

If this flow rate is to be varied, the second part 14 is rotated relative to the first part 12 about the axis X. In this condition, the hole 28*b* in the first gasket 58 moves away from the hole 28*c* defining an open condition which was creating a continuous flow line of the liquid. Now, the hole 28a in the base wall 54 of the second part 14, hole 28e in the base wall 54a of the mating attachment part 16 and the concentric hole 28c formed in the circular wall 26 of the first part 12 are not coaxial. The liquid arriving from the hole 28b of the first gasket 58 hence passes into the dosing groove 34 formed on the surface of the circular wall 26 of the first part 12. This liquid passes into the dosing groove 34 to fill it taking the liquid to the thorough hole 28c formed in the circular wall 26 of the first part 12. The liquid passes through this hole 28c of the circular wall 26 and passes into the dosing groove 34 formed on the other side of the circular wall 26, on reaching the hole 28d of the second gasket 60 positioned in the mating attachment part 16, it can pass through the tubular connector 20 and into the tubing line 24. The more the second part 14 is rotated to increase the distance of the thorough hole 28b of the gasket 58 from the hole 28c formed in the circular wall 26 of the first part 12, the greater the reduction in the flow rate of the liquid directed towards the hole 28d in the second gasket 60 positioned in the mating attachment part 16 and from thereto in the tubing line 24. By virtue of the at least one concentric dosing groove 34 provided on the both surfaces 68, 70 of the circular wall 26 of the first part 12 it is possible to regulate as well as control very precisely the quantity of medical liquid control flow to a patient in consonance with the peripheral scale 36 indicated on the side wall 32 of the first part 12. The flow rate regulation is also simple and reliable. Moreover, the present flow regulator 10 for regulating flow rate in a medical line having a smaller number of components than the scores of components being used in the contemporary flow regulator devices substantially reduces the production and storage cost.

The method of fabrication of the IV flow regulator 10 according to the invention comprises the following steps: moulding said first part 12, said second part 14 and said mating attachment part 16 within a first, second and third mould respectively; moulding said first gasket 58 and the second gasket 60 as whole with annular legs 72; positioning said first gasket 58 in the depression 62 formed integrally in the base wall 54 of said second part 14 in a position, the first surface 68b of said first gasket 58 facing the first part; positioning said second gasket 60 in the depression 62a formed integrally in the base wall 54a of said mating attachment part 16 in a position, the first surface 68d of said second gasket 60 facing the first part 12; fitting said first part, said second part 14 and said mating attachment part 16 to one another in a mutually rotatable way aligning the thorough holes 28 c, a, e, b, d made in said first part 12, said second part 14, said mating attachment part 16, said first gasket 58 and said second gasket 60, respectively, coaxially in a see through arrangement; fitting the first tubing line 22 to said inlet tubular connector 18 and second tubing line 24 to said outlet tubular connector 20.

Once the steps of moulding are completed, the first part 12 with the gasket 58 inter-positioned thereon, the second part 14 and the mating part 16 with the gasket 60 inter-positioned thereon are coupled to one another in a rotatable way. The steps of clamping, welding and auto-de clamping are carried out to ensure the smooth functioning and movement of the IV flow rate regulator 10. A uniform layer of silicon layer is applied to the second surface 70b and 70d of the first 58 and second gasket 60 to seal said gaskets 58, 60 in the depression 62 and 62a made in said first part 12 and said mating attachment part 16 respectively. The thorough holes made in the first part 12, second part 14, mating attachment part 16, first gasket 58 and second gasket 60 are preferably arranged co-axially in a see through arrangement while assembling the IV flow rate regulator 10.

The first part 12, second part 14 and said mating attachment part 16 are made preferably by injection moulding of suitable plastic material in a single piece. The first gasket 58 and second gasket 60 are made preferably by injection moulding of suitable elastomeric material. The side wall 32 of said first part 12 is marked integrally with a peripheral scale 36 in a circular fashion with the markings of units of measurements of the quantity flow of liquid that, in use, traverse the flow regulator 10 including the markings indicating the open and close position of the IV flow regulator 10. Further, the side skirt 30a of said second part 14 is marked integrally with a pointer 52. Following upon assembly, the pointer 52 marked integrally on the side skirt 30a of the second part 14 enables in co-operation with one or other of the peripheral scale 36 marked on the side wall 32 of the first part 12, or else with the wordings marked on said side of the first part 12, immediate visualization of the relative angular position selected by the user of the IV flow regulator 10 between the first part 12 and second part 14 corresponding to the regulation of flow selection. The setting can be made in an extremely smooth, easy and convenient way with the feel of the side skirts 30 and 30a of the first 12 and second part 14 even by use of just one hand.

To limit the rotation of coupled first 12 and second part 14 to about one complete turn, retainers in the form of projections/protuberance 44, 46 are provided on said first and second part 14 respectively. The projections/protuberances 44, 46 on the first part 12 and second part 14 also controls the open and off operations of the IV flow rate regulator 10.

The fabrication of the IV flow rate regulator 10 according to the invention may be obtained using simplified equipment as regards moulding of its components. Once assembled, the components of IV flow regulator 10 functions to both set and maintain the flow rate of an IV solution in IV therapy administration system. Thus, the present invention encompasses design features that allow for the manufacturing of a highly accurate and precision dosage flow control regulator using high volume molding and automated assembly.

According to a preferred embodiment of the present invention, the scales 36 in the outer perimeter of the second part 14 and the pointer 52 on the outer perimeter of the first part 12 may be formed by impressions and include the provisions for integrated impressions. The scales 36 may be integrated with wordings indicating the condition of the open and/or off of the IV flow rate regulator 10 and include different units of measurements for delivery of fluids being administered to a patient. The side skirt shapes 30 and 30a forming the part of the first 12 and second 14 parts, is also designed to facilitate manipulation and regulation of the IV flow rate regulator 10 conveniently with just one hand.

Although, the invention has been described with reference to certain specific embodiments and examples, it would be appreciated by those skilled in the art that the invention may be embodied in many forms without departing from the broader spirit and scope of the invention as set forth in the invention. Thus, variations of preferred embodiments as disclosed may become apparent to those of ordinary skill in the art upon reading the foregoing description.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. The specification and drawings, therefore, are to be regarded in an illustrative rather than a restrictive manner without departing from the spirit and scope of the invention, the invention resides in the claims hereinafter appended.

LIST OF REFERENCE NUMERALS

10 IV flow rate regulator
12 first part
14 second part
16 mating attachment part
18 inlet tubular connector
20 outlet tubular connector
22 first tubing line
24 second tubing line
26 circular wall
28 hole
28a hole in the second part
28b hole in the first gasket
28c hole in the first part
28d hole in the second gasket
28e hole in the mating attachment part
30 side skirt of the first part
30a side skirt of the second part
32 side wall of the first part
32a side wall of the second part
34 dosing groove
36 peripheral scale
38 inner surface
40 wall (A)
42 wall (B)
44 first projection
46 second projection
50 control dial
52 pointer
54 base wall of the second part
54a base wall of the mating attachment part
56 central bore of the second part
56a central bore of the mating attachment part
56b central bore of the first gasket
56d central bore of the second gasket
58 first gasket
60 second gasket
62 depression of the second part
62a depression of the mating attachment part
64 wall (C)
66 wall (D)
68 first surface of the first part
68b first surface of the first gasket
68d first surface of the second gasket
70 second surface of the first part
70b second surface of the first gasket
70d second surface of the second gasket
72 annular legs
74 inner periphery
76 outer periphery
78 recess
80 projection
82 connecting element
84 top wall
86 wall (E)
88 wall (F)
90 wall (G)
92 male luer connector
94 female luer connector
96 Y site
98 luer cap
100 luer lock
102 leg

The invention claimed is:

1. A method of fabrication of an IV flow rate regulator comprising:
a first part, a second part with at least one integrated outlet tubular connector and a mating attachment part with at least one integrated inlet tubular connector, said first part, said second part, and said mating attachment part made of a molded plastic material and being coupled to one another in a rotatable manner about an axis of rotation with a first gasket made of an elastomeric material being inter-positioned in a depression integrally made in a base wall of said second part, a second gasket made of the elastomeric material being inter-positioned in a depression integrally made in a base wall of said mating attachment part, at least one dosing passage groove being provided between said first gasket and said second gasket, said dosing groove opening progressively the communication between said at least one integrated inlet tubular connector and said at least one integrated outlet connector by relative rotation of said first part and said second part, said method comprising the steps of:
molding said first part, said second part and said mating attachment part within a first, second and third mold respectively;
molding said first gasket and the second gasket as whole with annular legs;
positioning said first gasket in the depression formed integrally in the base wall of said second part in a position, a first surface of said first gasket facing the first part;
positioning said second gasket in the depression formed integrally in the base wall of said mating attachment part in a position, a first surface of said second gasket facing the first part;
fitting said first part, said second part and said mating attachment part to one another in a mutually rotatable way aligning thorough holes made in said first part, said second part, said mating attachment part, said first gasket and said second gasket coaxially in a see through arrangement; and
fitting a first tubing line to said at least one integrated inlet connector and a second tubing line to said at least one integrated outlet connector.

2. The method according to claim 1, further comprising the steps of thereafter clamping, welding and auto de-clamping of said first part, second said part and said mating attachment to one another in a mutually rotatable manner.

3. The method according to claim 1, comprising the steps of applying a uniform layer of silicon spray to facilitate sealing of a second surface of said first gasket and said second gasket.

4. The method according to claim 1, wherein said first part, said second part and said mating attachment part are made by injection moulding of the plastic material in a single piece.

5. The method according to claim 1, wherein said first gasket and said second gasket are made by injection moulding of the elastomeric material.

6. A method of fabrication of an IV flow rate regulator comprising:
a first part, a second part with at least one integrated outlet tubular connector and a mating attachment part with at least one integrated inlet tubular connector, said first part, said second part, and said mating attachment part made of a molded plastic material and being coupled to one another in a rotatable manner about an axis of rotation with a first gasket made of an elastomeric material being inter-positioned in a depression integrally made in a base wall of said second part, a second gasket made of the elastomeric material being inter-positioned in a depression integrally made in a base wall of said mating attachment part, at least one dosing passage groove being provided between said first gasket and said second gasket, said dosing groove opening progressively the communication between said said at least one integrated inlet tubular connector and said at least one integrated outlet connector by relative rotation of said first part and said second part, wherein said first gasket and said second gasket comprises a plurality of annular legs projecting radially from an outer periphery of the first gasket in addition with at least one leg projecting radially inward from an inner periphery of said first gasket and said second gasket;

said method comprising the steps of:

molding said first part, said second part and said mating attachment part within a first, second and third mold respectively;

molding said first gasket and the second gasket as whole with the plurality of annular legs;

positioning said first gasket in the depression formed integrally in the base wall of said second part in a position, a first surface of said first gasket facing the first part;

positioning said second gasket in the depression formed integrally in the base wall of said mating attachment part in a position, a first surface of said second gasket facing the first part;

fitting said first part, said second part and said mating attachment part to one another in a mutually rotatable way aligning thorough holes made in said first part, said second part, said mating attachment part, said first gasket and said second gasket coaxially in a see through arrangement; and fitting a first tubing line to said at least one integrated inlet connector and a second tubing line to said at least one integrated outlet connector.

* * * * *